(12) United States Patent
Shimokawa et al.

(10) Patent No.: US 8,759,012 B2
(45) Date of Patent: Jun. 24, 2014

(54) METHOD OF DETERMINING DOSE AND ADMINISTRATION OF STATIN

(75) Inventors: Hiroaki Shimokawa, Sendai (JP); Shin-ichi Tanaka, Sendai (JP)

(73) Assignee: Tohoku University, Sendai-Shi (JP)

( * ) Notice: Subject to any disclaimer, the term of this patent is extended or adjusted under 35 U.S.C. 154(b) by 0 days.

(21) Appl. No.: 13/316,246

(22) Filed: Dec. 9, 2011

(65) Prior Publication Data

US 2013/0065226 A1 Mar. 14, 2013

(30) Foreign Application Priority Data

Sep. 12, 2011 (JP) .................................. 2011-197906

(51) Int. Cl.
| | | |
|---|---|---|
| *G01N 33/53* | (2006.01) | |
| *G01N 33/00* | (2006.01) | |
| *G01N 33/573* | (2006.01) | |
| *C12Q 1/48* | (2006.01) | |

(52) U.S. Cl.
USPC ............... 435/7.1; 435/7.24; 435/7.4; 435/15

(58) Field of Classification Search
None
See application file for complete search history.

(56) References Cited

PUBLICATIONS

Chen G. et al. Molecular & Cellular Proteomics 1.4 (2002) pp. 304-313.*
Cheung V.G. et al. Nature Genetics, vol. 33 (Mar. 2003), pp. 422-425.*
Cobb J.P. et al. Crit Care Med 2002 vol. 30, No. 12, pp. 2711-2721.*
Enard W. et al. Science (Apr. 2002) vol. 296, pp. 340-343.*

* cited by examiner

*Primary Examiner* — Stephen Kapushoc
(74) *Attorney, Agent, or Firm* — Birch, Stewart, Kolasch & Birch, LLP (57) ABSTRACT

The object of the present invention is to provide a method of determining the dose and/or administration of statins to a patient suffering from a cardiovascular disease.
The object is achieved by the method of determining the dose and/or administration of statins to a patient suffering from a cardiovascular disease comprising Step (1) of measuring the intracellular SmgGDS expression level of a patient suffering from a cardiovascular disease before and after administration of statin; and Step (2) of determining the type and/or the dose of statin for the patient in reference to the SmgGDS expression level measured in the Step (1).

5 Claims, 9 Drawing Sheets
(8 of 9 Drawing Sheet(s) Filed in Color)

METHOD OF DETERMINING DOSE AND ADMINISTRATION OF STATIN

BACKGROUND OF THE INVENTION

1. Field of the Invention

The present invention relates to a method of determining the dose and administration of statin.

2. Description of the Related Art

HMG-CoA reductase inhibitors (statins) are potent cholesterol-lowering drugs that are being widely used in clinical practice for the primary and secondary prevention of coronary artery diseases (see Referenced Patent Publications (RPPs) 1 and 2 as described hereinafter). Additionally, it has been reported in recent years that statins protectively act on cardiovascular diseases beyond their lipid-lowering action (so-called pleiotropic effects) and hence are currently being highlighted (see NPLs 3 and 4). The pleiotropic effects of statins could be mediated by reduced synthesis of isoprenoids that playa role of functioning for the post-translational regulation of intracellular proteins (see RPP 1). In other words, the activity of small GTP-binding proteins such as Rho, Rac and Ras, of which membrane localization and GTPase activity are dependent on isoprenylation of the proteins, is believed to mediate the pleiotropic effects of statins (see RPPs 5 and 6).

The present inventors have previously demonstrated that low-dose statins (atorvastatin and pravastatin, 20 mg day$^{-1}$ for 1 week) significantly inhibit Rac1 activity only without suppressing the RhoA/Rho-kinase activity in circulating leucocytes in normal and healthy volunteers (see RPP 7). It is known that Rac1 plays a crucial role in generating reactive oxygen species (ROS). Since it has been reported that Rac1 increases ROS production and thereby develops myocardial hypertrophy and ventricular remodeling, it has been suggested that Rac1 may be an important mediator of cardiovascular hypertrophy (see RPP 8).

It has been reported that simvastatin inhibits Rac1-mediated nicotinamide-adenine dinucleotide phosphate (NADPH) oxidase activity in the heart and vascular smooth muscle in mouse models having angiotensin II (AngII)-induced cardiac hypertrophy (see RPPs 9 and 10). These findings are further supported by analysis of human heart tissues and it has been reported that statins suppress ROS production by way of Rac1 activation (see RPP 11). Thus, the present inventors have proposed that the pleiotropic effects of low-dose statins are mediated mainly through inhibition of the Rac1 pathway rather than that of the Rho/Rho-kinase pathway (see RPP 7).

The small GTP-binding protein GDP dissociation simulator (SmgGDS) is one belonging to the only guanine nucleotide exchange factor (GEF) in the armadillo (ARM) family of proteins (see RPPs 12 and 13). Recently, the role of GEF in the development of cardiovascular diseases has been highlighted (see RPPs 14 through 16). It has also been reported that purified SmgGDS interacts with the small GTPase C-terminal polybasic region (PBR) and activates RhoA and RhoC by its GEF function (see RPP 17). Furthermore, it has been reported that the PBR of Rac1 has a functional nuclear localization signal (NLS) sequence which is not present in RhoA (see RPP 13). Rac1 with the NSL will accompany SmgGDS into the nucleus and thereby be degraded by the proteasome system (see RPP 18).

Referenced Patent Publication (RPP) 1 is Scandinavian Simvastatin Survival Study Group. Randomized trial of cholesterol lowering in 4444 patients with coronary heart disease: the Scandinavian Survival Study (4S). Lancet 344, 1383-1389 (1994); RPP2 is Levine, G. N., Keaney, Jr., J. F. & Vita, J. A., N. Engl. J. Med. 332, 512-521 (1995); RPP3 is Davignon J., Circulation 109, 39-43 (2004); RPP4 is Rikitake, Y., Liao, J. K., Circ. Res. 97, 1232-1235 (2005); RPP5 is Hall, A., Science 279, 509-514 (1998); RPP6 is Takemoto, M., Liao JK., Arterioscler. Thromb. Vasc. Biol. 21, 1712-1719 (2001); RPP7 is Rashid M. et al., Circ. J. 73, 361-370 (2009); RPP8 is Brown J. H., Del Re, D. P., Sussman, M. A., Circ. Res. 98, 730-742 (2006); RPP9 is Takemoto M. et al., J. Clin. Invest. 108, 1429-1437 (2001); RPP10 is Wassmann, S. et al., Mol. Pharmacol. 59, 646-654 (2001); RPP11 is Maack, C. et al., Circulation 108, 1567-1574 (2003); RPP12 is Yamamoto, T. et al., J. Biol. Chem. 265, 16626-16634 (1990); RPP13 is Williams, C. L., Cell signal. 15, 1071-1080 (2003); RPP14 is Guilluy, C. et al., Nat. Med. 16, 183-190 (2010); RPP15 is Sauzeau, V., Sevilla, M. A., Montero, M. J. & Bustelo, X. R., J. Clin. Invest. 120, 315-330 (2010); RPP16 is Sauzeau, V. et al., Nat. Med. 12, 841-845 (2006); RPP17 is Hamel, B. et al., J. Biol. Chem. 286, 12141-12148 (2011); RPP18 is Lannning, C. C. et al., J. Biol. Chem. 279, 44197-44210 (2004).

SUMMARY OF THE INVENTION

As described above, it has been believed that a certain relationship exists between the activities of small GTP-binding proteins such as Rho, Rac and Ras and the pleiotropic effects of statins. However, the molecular mechanisms of the pleiotropic effects of low-dose statins still remain to be elucidated in a large number of aspects.

Besides, the present inventors have suggested the possibility that the pleiotropic effects of low-dose statins are mainly mediated through inhibition of the Rac1 pathway. However, the molecular mechanisms of the selective inhibition of the Rac1 signaling pathway by low-dose statins remain to be elucidated. Additionally, due to this fact, most statins that are being clinically used are being consumed as medicines for treating hypercholesterolemia and the probability of application of statins to cardiovascular diseases such as cardiovascular hypertrophy has not yet been discussed satisfactorily.

In view of the above-identified circumstances, an object of the present invention is therefore to provide a method of determining the dose and administration of statin to a patient suffering from a cardiovascular disease by clarifying at least a part of the molecular mechanism of the selective inhibition of the Rac1 signaling pathway by means of statins.

Figure 6:
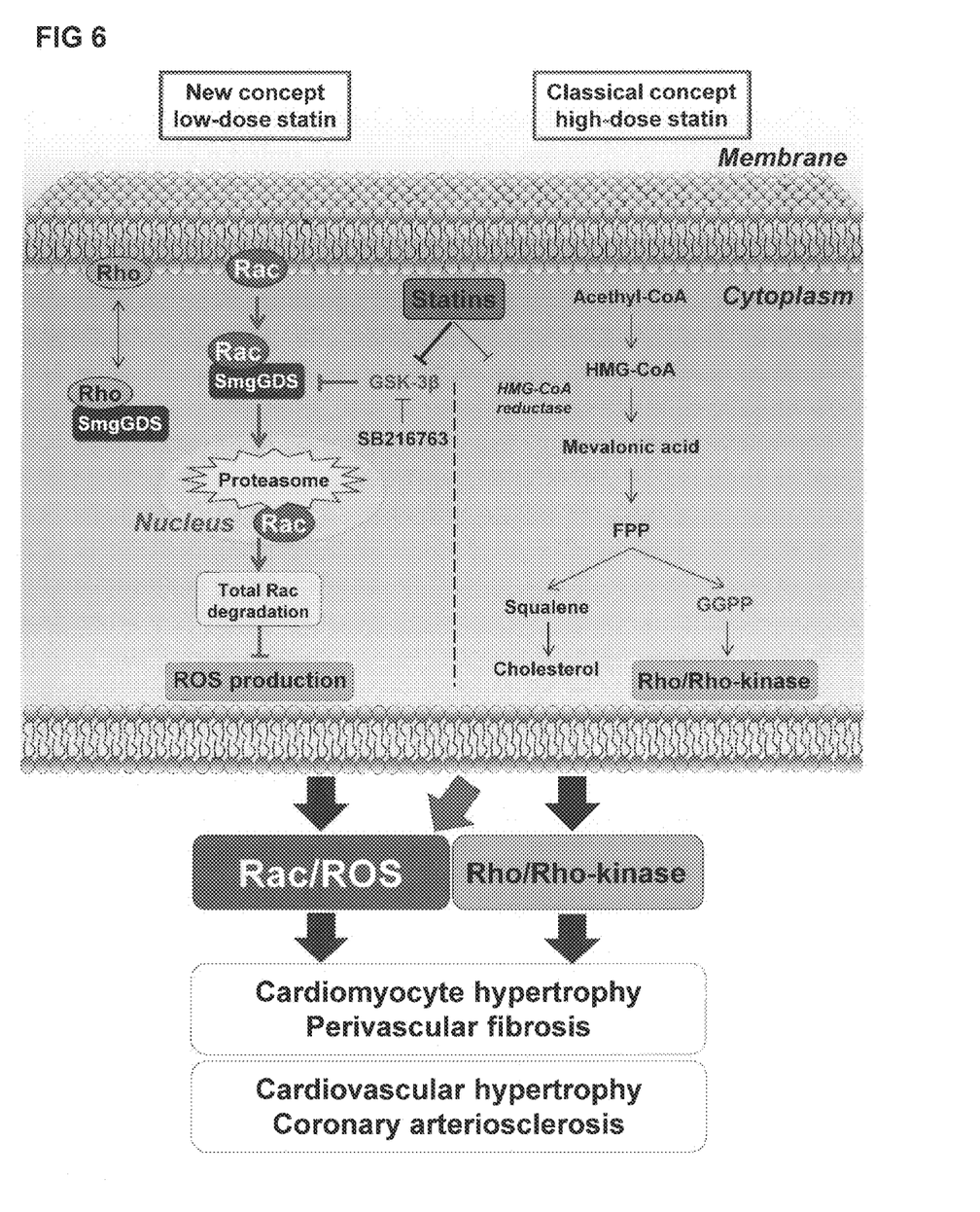
FIG. 6 schematically illustrates the novel molecular mechanisms of the pleiotropic effects of statins. Low-dose statins increase SmgGDS through GSK-3β. The increased SmgGDS binds to Rac1 and transports it to the nucleus. The Rac1 transported to the nucleus is degraded by proteasome. Rac1 degradation causes decreased ROS production. Finally, Rac1-mediated decrease in ROS production reduces cardiomyocyte hypertrophy and fibrosis, and further cardiac hypertrophy, which achieves the pleiotropic effects of statins.

The present inventors strenuously examined the findings that had been already obtained, and attained to a hypothesis that SmgGDS would play a crucial role in the molecular mechanisms relating to the selective inhibition of the Rac1 signaling pathway by means of statins. Then, the present inventors' results obtained due to their intensive research and development efforts are those providing the first evidence that SmgGDS plays a crucial role in animals and humans in terms of the molecular mechanisms of pleiotropic effects of statins that increase Rac1 decomposition in the nucleus. The molecular mechanisms are schematically illustrated in FIG. 6.

Firstly, statins enhances SmgGDS expression in cytoplasm. Secondly, SmgGDS binds to Rac1 and then transports it to the nucleus. Thirdly, Rac1 is degraded by nuclear proteasomes. Fourthly, the degradation of Rac1 induces a decrease of ROS production. Finally, the decrease of ROS production induces the cardiovascular protection, that is, the pleiotropic effects of statins on treatment and prevention of cardiovascular diseases including cardiovascular hypertrophy, cardiomyocyte hypertrophy, perivascular fibrosis and coronary arteriosclerosis (FIG. 6). The present invention is one completed based on these findings.

Thus, according to the present invention, there is provided a method of determining the dose and/or administration of statins to a patient suffering from a cardiovascular disease comprising Step (1) of measuring the intracellular SmgGDS expression level of a patient suffering from a cardiovascular disease before and after administration of statin; and Step (2) of determining the type and/or the dose of statin for the patient in reference to the SmgGDS expression level measured in the Step (1).

The cardiovascular disease preferably used for the purpose of the present invention is cardiovascular hypertrophy, cardiomyocyte hypertrophy, cardiovascular fibrosis, coronary arteriosclerosis, hypertension or heart failure.

The statins preferably used for the purpose of the present invention are selected from a group consisting of atorvastatin, dihydrocompactin, bervastatin, carvastatin, cerivastatin, crilvastatin, dalvastatin, fluvastatin, glenvastatin, fluindostatin, velostatin, lovastatin, mevastatin, compactin, pitavastatin, pravastatin, rivastatin, rosuvastatin, simvastatin, sirrivastatin, CI-981 and pharmacologically acceptable salts thereof.

The reference preferably used for the purpose of the present invention is such that the SmgGDS expression level after administration of statins is 1.4 times or more compared with the SmgGDS expression level before the administration.

Thus, with the method of the present invention, it is possible to determine the dose and/or administration of statin by determining the type and/or the dose of statin to be used to a patient suffering from a cardiovascular disease. The method of the present invention provides an advantage that the dose and administration of statin for treatment can be quickly and objectively determined by confirming the intracellular SmgGDS expression level without checking the symptom of the disease.

BRIEF DESCRIPTION OF THE DRAWINGS

The patent or application file contains at least one color drawing. Copies of this patent or patent application publication with color drawing will be provided by the USPTO upon request and payment of the necessary fee.

FIG. 4A illustrates that ameliorating effects of statins are absent in SmgGDS-deficient mice with AngII-induced cardiac diastolic dysfunction. It represents the results of echocardiography in control (−), AngII-infused mice treated with either atorvastatin (AngII+ATOR, 10 mg kg$^{-1}$ day$^{-1}$) or pravastatin (AngII+PRA, 50 mg kg$^{-1}$ day$^{-1}$), and AngII-infused mice (with administered vehicle, AngII(+)). FIG. 4A illustrates the results for relative wall thickness of the heart. The results are expressed as mean±s.e.m.

FIG. 4B illustrates that ameliorating effects of statins are absent in SmgGDS-deficient mice with AngII-induced cardiac diastolic dysfunction. It represents the results of echocardiography in control (−), AngII-infused mice treated with either atorvastatin (AngII+ATOR, 10 mg kg$^{-1}$ day$^{-1}$) or pravastatin (AngII+PRA, 50 mg kg$^{-1}$ day$^{-1}$), and AngII-infused mice (with administered vehicle, AngII(+)). FIG. 4B illustrates the results for fractional shortening of the left ventricular internal diameter (n=10). The results are expressed as mean±s.e.m.

FIG. 4C illustrates that ameliorating effects of statins are absent in SmgGDS-deficient mice with AngII-induced cardiac diastolic dysfunction. It represents the results of echocardiography in control (−), AngII-infused mice treated with either atorvastatin (AngII+ATOR, 10 mg kg$^{-1}$ day$^{-1}$) or pravastatin (AngII+PRA, 50 mg kg$^{-1}$ day$^{-1}$), and AngII-infused mice (with administered vehicle, AngII(+)). FIG. 4C illustrates the results for E/A ratio (n=10). The results are expressed as mean±s.e.m.

FIG. 4D illustrates that ameliorating effects of statins are absent in SmgGDS-deficient mice with AngII-induced cardiac diastolic dysfunction. It represents the results of echocardiography in control (−), AngII-infused mice treated with either atorvastatin (AngII+ATOR, 10 mg kg$^{-1}$ day$^{-1}$) or pravastatin (AngII+PRA, 50 mg kg$^{-1}$ day$^{-1}$), and AngII-infused mice (with administered vehicle, AngII(+)). FIG. 4D illustrates the results for heart rate (n=10). The results are expressed as mean±s.e.m.

FIG. 5A illustrates that statins up-regulate SmgGDS level in humans. It represents the protein levels of SmgGDS of circulating human leukocyte. FIG. 5A illustrates that the SmgGDS level was significantly increased after administration of either pravastatin (PRA, 20 mg day$^{-1}$) or atorvastatin (ATOR, 20 mg day$^{-1}$) for 2 weeks if compared with the pre-administration level (n=20). The results are expressed as mean±s.d.

FIG. 5B illustrates that statins up-regulate SmgGDS level in humans. It represents the correlation between SmgGDS changes and LDL-cholesterol changes in humans (n=20).

FIG. 5C illustrates that statins up-regulate SmgGDS level in humans. It represents the correlation between SmgGDS changes and LDL-cholesterol changes in humans (n=20).

FIG. 5D illustrates that statins up-regulate SmgGDS level in humans. It represents the correlation between SmgGDS changes and MDA-LDL-cholesterol changes in humans (n=20).

FIG. 5E illustrates that statins up-regulate SmgGDS level in humans. It represents the correlation between SmgGDS changes and MDA-LDL-cholesterol changes in humans (n=20).

DESCRIPTION OF THE PREFERRED EMBODIMENTS

Now, the present invention will be described in greater detail by referring to the accompanying drawings.

The present invention provides a method of determining the dose or administration of statin, or both of them, to a patient suffering from a cardiovascular disease, the method comprising:

Step (1) of measuring the intracellular SmgGDS expression level of a patient suffering from a cardiovascular disease before and after administration of statin (to be referred to as "Step (1)" hereinafter); and Step (2) of determining the type and/or the dose of statin for the patient in reference to the SmgGDS expression level measured in the Step (1) (to be referred to as "Step (2)" hereinafter).

Cardiovascular diseases are a generic term for various ailments of hearts. Since the method of the present invention is based on the fact that statins reduce reactive oxygen species (ROS) as one of the pleiotropic effects of statins, the cardiovascular diseases that can be treated by the method of the present invention are preferably cardiovascular diseases attributable to ROS such as cardiovascular hypertrophy, cardiomyocyte hypertrophy, cardiovascular fibrosis, coronary arteriosclerosis, hypertension and heart failure.

Patients suffering from a cardiovascular disease who can be treated by the method of the present invention are not particularly subjected to any limitation. Examples of such patients include those who are currently suffering from cardiovascular diseases, those who have previous history of a cardiovascular disease, those who are genetically or constitutionally liable to a cardiovascular disease, and those who are liable to a cardiovascular disease on the basis of some other disease the patient currently has. Furthermore, the stages of progression of a cardiovascular disease are not particularly subjected to any limitation.

Statins are also referred to as HMG-CoA reductase inhibitors and are known as pharmaceutical agents that inhibit HMG-CoA reductase, which is an enzyme catalyzing the reaction of converting HMG-CoA into mevalonic acid on the Rho/Rho-kinase pathway as shown in FIG. 6. A variety of statins are known to date and include not only those that are currently being clinically employed but also those whose sale or development has been suspended and those that are on a stage of clinical experiment. Statins that are targets of the present invention are not subjected to any limitation and include all that are referred to as statins. Examples of statins preferably used for the purpose of the present invention include atorvastatin, dihydrocompactin, bervastatin, carvastatin, cerivastatin, crilvastatin, dalvastatin, fluvastatin, glenvastatin, fluindostatin, velostatin, lovastatin, mevastatin, compactin, pitavastatin, pravastatin, rivastatin, rosuvastatin, simvastatin, sirrivastatin, CI-981 and pharmacologically acceptable salts thereof.

Statins referred to in the present specification are not limited to statins as compounds but include statin pharmaceuticals prepared by combining a statin and an excipient. Examples of statin pharmaceuticals include Lipitor tablets containing atorvastatin salt as an active ingredient and Mevalotin tablets containing pravastatin salt as an active ingredient.

Statins have been clinically employed to date as therapeutic medicaments of hyperlipemia and hypercholesterolemia but not as therapeutic medicaments of cardiovascular diseases such as cardiovascular hypertrophy and cardiomyocyte hypertrophy. In view of these circumstances, the present invention is one conceived with an objective of accelerating the clinical application of statins to cardiovascular diseases. Therefore, the present invention is a breakthrough one because it is successfully completed in pursuit of further possibilities of clinical application of statins. The present invention broadens the scope of therapeutic options for treating cardiovascular diseases and hence is very beneficial to both patients and doctors.

In Step (1) of the method of the present invention, the intracellular SmgGDS expression level of a patient suffering from a cardiovascular disease before and after administration of statin is measured. The SmgGDS expression level can be measured by applying any methods of quantifying the proteins in cells that is well known to those skilled in the art. For example, a method of taking a biological sample from a patient suffering from a cardiovascular disease, isolating cells in the biological sample, homogenizing the cells to obtain a lysate containing SmgGDS and then quantifying the SmgGDS can be employed.

More specifically, venous blood is sampled from a patient suffering from a cardiovascular disease in fasting conditions and then leukocytes are isolated from the sample blood. Then, the isolated leukocytes are washed a few times with an appropriate buffer solution and subsequently, the washed leukocytes are added to a lysis buffer followed by being sonicated to obtain a cell lysate. The obtained cell lysate is subjected as sample to a western blot analysis using an anti SmgGDS antibody and the like to quantify the SmgGDS in the leukocytes. Alternatively, the cell lysate may be subjected to subcellular fractionation and the uneven distribution of SmgGDS in cells may be examined.

The SmgGDS expression level is measured at least twice before administration of statins, for example, immediately before administration of statins and after administration of statins, for example, 24 hours after administration of statins, by using a biological sample taken from a patient suffering from a cardiovascular disease.

In Step (2) of the method of the present invention, the type or the dose of statin, or both of them, to be administered to the patient suffering from a cardiovascular disease are determined in reference to the SmgGDS expression level measured in Step (1). The present invention is intended to encourage clinical applications of statins to patients suffering from cardiovascular diseases on the basis of the effect of statins of reducing ROS. The ROS-reduced effect of statins is achieved due to the molecular mechanisms that statins inhibit GSK-3β so that SmgGDS targeted by GSK-3β proliferates in cells and its activity is enhanced. In other words, SmgGDS transports Rac1 to the nucleus. Rac1 is then degraded by nuclear proteasomes. Degradation of Rac1 causes decreased ROS production. Rac1-mediated decrease in ROS production reduces cardiovascular hypertrophy, since elevated ROS production induces cardiomyocyte hypertrophy and perivascular fibrosis. Therefore, if the intracellular SmgGDS expression level is raised by administering a statin to a cardiovascular disease patient, an improvement in the patient's cardiovascular disease can be expected.

With the method of the present invention, the intracellular SmgGDS expression level before administration of a statin is compared with the SmgGDS expression level after the administration. If the expression level after the administration represents no difference or falls from the expression level before the administration, therapeutic options containing changing the type of statin to be administered and/or increasing the statin dose can be applied. Which alternative is to be adopted may be decided by considering the number of times and the period of statin administration and the like. For instance, the dose of statin may be increased first and, if no difference is observed in the intracellular SmgGDS expression level before and after the administration, then it is determined that a different statin should be administered. If, to the contrary, an increase is observed in the intracellular SmgGDS expression level after the statin administration if compared with before the statin administration, it is determined that the dose of statin should not be changed.

As described in the examples, which will be described hereinafter, there are instances where no increase of SmgGDS is observed in some subjects after administering pravastatin with a dose of 10 mg, although a decrease in the LDL-cholesterol level is observable. If such is the case, neither any increase of statin dose nor switch to a different statin is conceivable in reference to an increase or decrease in the LDL-cholesterol level so that no statin can be administered with an effective dose to the patient suffering from a cardiovascular disease. In other words, an appropriate statin can be administered with an effective dose to a patient suffering from a cardiovascular disease in reference to the increase or decrease in intracellular SmgGDS expression level only by employing the method of the present invention.

Figure 5:
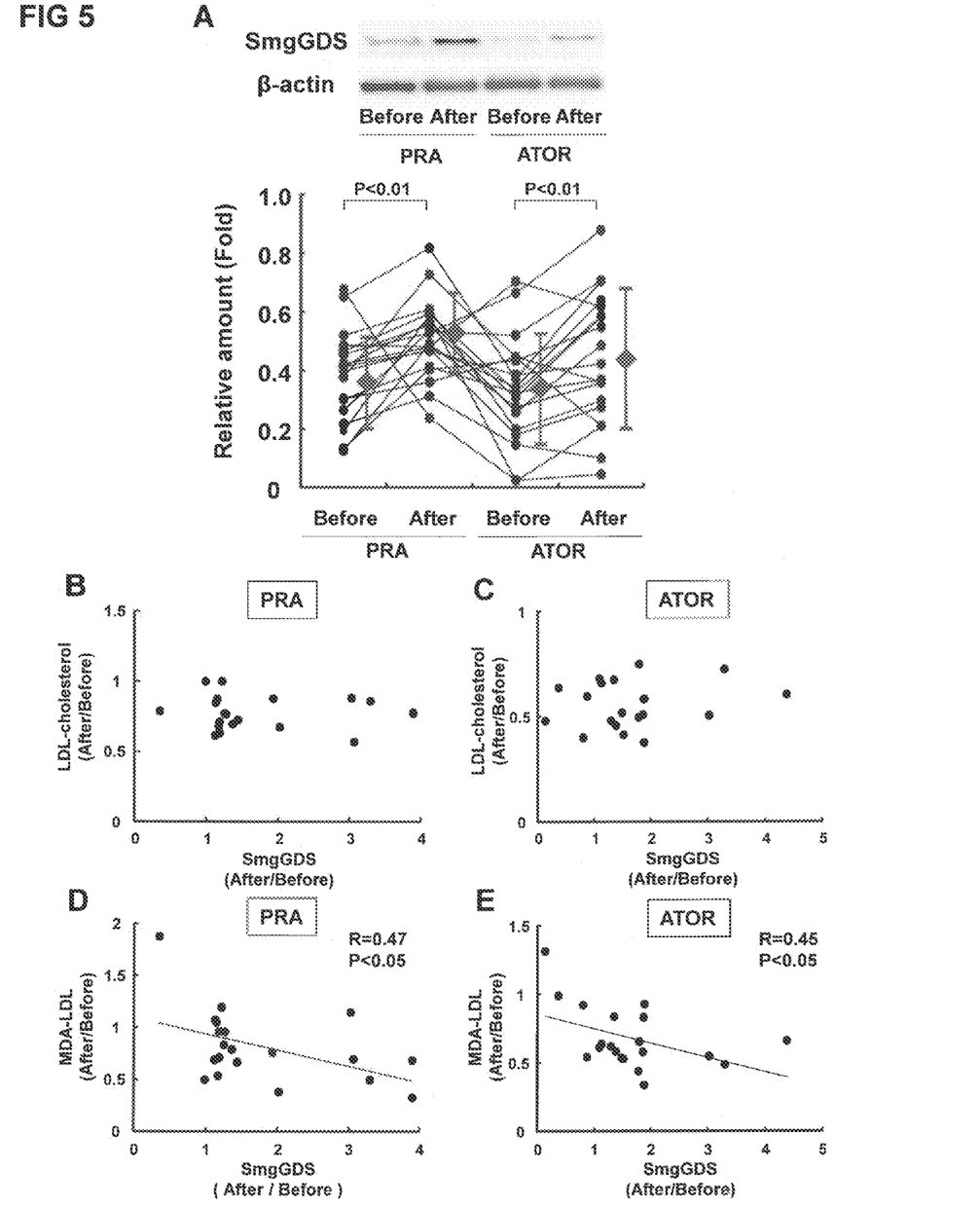

In view of the results illustrated in FIG. 5A, which demonstrates that the intracellular SmgGDS expression level can be enhanced by more than 1.4 times by increasing the statin dose from 10 mg to 20 mg, the type and dose of statin to be administered is preferably determined for the purpose of the present invention in reference to if the SmgGDS expression level after administering the statin is 1.4 times or more compare with the SmgGDS expression level before administering the statin.

The method of the present invention does not eliminate incorporating some other steps before or after of each of the Steps (1) and (2) provided that the object of the present invention is achievable by such incorporation. While the type and dose of statin that are beneficial to a cardiovascular disease patient can be determined by the method of the present invention, the type and dose of statin can also be determined by combining the method of the present invention and various numerical values and symptoms that can be used as indexes of the stage of cardiovascular disease.

Those skilled in the art can comprehend the usefulness of the method of the present invention by considering the various results of the experiments in the examples that are described hereinafter. For example, the obtained results include one that statins enhanced SmgGDS expression and Rac1 degradation, and increased ROS production in cultured endothelial cells independent of mevalonic acid or Rho/Rho-kinase pathway; one that the cardiovascular protective effects of statins were absent in SmgGDS-deficient mice; one that statins significantly increased SmgGDS expression in normal healthy individuals; one that SmgGDS expression levels and oxidative stress markers represented significant negative correlation; and one that no correlation was observed between total cholesterol or LDL-cholesterol and oxidative stress markers. By referring to those results, those skilled in the art can recognize the effective and novel active mechanism of statins through enhancement of Rac1 degradation in addition to inhibition of mevalonic acid and Rho/Rho-kinase pathways. Further, based on the above experiments, those skilled in the art can recognize that the method of the present invention is an effective and novel method.

Now, the present invention will be described in greater detail by way of examples, although the present invention is by no means limited to the examples.

EXAMPLES

1st: Summary of Experiment Methods

HUVEC was treated with statins for 24 hours and then collected. After the treatment, lysis buffer was added to the cells and then subjected to sonication. Protein expression levels were measured by western blot analysis. The subcellular fractionation was performed by a commercially available cell compartment kit. The transfection of multiple siRNA duplexes for SmgGDS was conducted according to Thill et al.'s literature (Thill, R., Campbell, W. B., Williams, C. L., J. Cell Biol. 104, 1760-1770 2008)). After knocking down SmgGDS in HUVEC by siRNA, the Rac1 expression level and the AngII-induced ROS production were measured according to Sato et al.'s literature (Satoh, K. et al., Nat. Med. 15, 649-656 (2008)). SmgGDS deficient mice were obtained from Research Institute, Osaka Medical Center for Cancer and Cardiovascular Diseases (see Takakura, A, et al., Mol. Biol. Cell 11, 1875-1886 (2008)). An AngII-induced cardiovascular hypertrophy model in mice was produced according to Yagi et al.'s literature (Yagi, S. et al., Circ. Res. 102, 68-76 (2008)). Statins were administered to mice by gavage every day for 2 weeks. After 2 weeks of sustained AngII administration by means of osmotic pump, the present inventors observed the left ventricular function and measured the weight of the heart of each mouse by means of an ultrasound imaging system. Histological studies were conducted for the determination of cross section area, wall thickness and fibrosis in a manner as described in the above cited Yagi et al.'s literature. A human study was performed as a single center, randomized crossover study at the Tohoku University Hospital, Japan. A daily dose of 20 mg atorvastatin or a daily dose of 20 mg paravastatin was administered randomly to a total of 20 healthy subjects for 2 weeks. After a 2 weeks washout period, the subjects were switched to take an alternative medicine for additional 2 weeks. Venous blood was collected in fasting conditions to measure the lipid profiles, the SmgGDS expression level in PMNL and drug safety before the treatment and 24 hours after the last intake of a statin. Leukocytes were isolated according to the method described in Liu et al.'s literature (Liu, P. Y., Chen, J. H., Lin, L. J., Liao, J. K., J. Am. Coll. Cardiol. 49, 1619-1624 (2007)) with slight modification.

2nd: Details of Experiments

1. Cell Culture and Drug Treatment

Human umbilical venous endothelial cells (HUVEC) (Takara Bio Inc., Otsu, Japan) were incubated at 37° C. in 5% $CO_2$ in endothelial growth medium (EGM-2, Lonza) for 24 hours. Then, the cells were treated with different concentrations (1-30 µM) of each statin (atorvastatin and pitavastatin), GSK-3β inhibitor (lithium chloride, Sigma) or Rho-kinase inhibitor (hydroxyfasudil) for 24 hours. The present inventors co-treated HUVEC with statins and farnesyl pyrophosphate (Sigma) or geranylgeranyl pyrophosphate (Sigma) for 24 hours or the proteasome inhibitor MG-132 (Calbiochem) for 14 hours. After treating the cells with each drug, they were washed twice with ice-cold phosphate-buffered saline (PBS) and then sonicated after adding lysis buffer. Subcellular fractionation was performed by Qproteome cell compartment kit (Qiagen).

2. Western Blot Analysis

To quantify the expression levels of RhoA, Rac1 and SmgGDS in HUVEC and in human PMNL, an equal number of protein samples were loaded on SDS-PAGE gel and transferred into PVDF membranes (GE Healthcare). Then, the transferred PVDF membranes were immunoblotted with anti-RhoA (Santa Cruz), anti-Rac1 (Millpore), anti-SmgGDS (BD transduction Lab.), anti-β-actin (Sigma), anti-GAPDH (Santa Cruz), anti-TIM23 (BD transduction Lab.) and anti-LAMIN A/C (BD transduction Lab.). After incubating with horseradish-peroxidase-conjugated rabbit anti-mouse, goat anti-rabbit or donkey anti-goat IgG antibody, blots were visualized by means of an enhanced chemiluminescence system (ECL Western Blotting Detection Kit, GE Healthcare). Densitometric analysis was performed by Image J (NIH) Software.

3. Transfection of siRNA into HUVEC

Multiple siRNAs duplexes specific to SmgGDS were purchased from Qiagen. A functional non-targeting siRNA that was bioinformatically designed by Qiagen was used as a control. Either 10 nM control siRNA or 10 nM siRNA that was specific to SmgGDS was transfected into HUVEC with HiPerFect transfection Reagent (Qiagen). After 72 hour post-transfection, the cells were analyzed by either Wester blot or ROS analysis.

4. Reactive Oxygen Species Analysis

Intracellular ROS production in HUVEC was measured according to the description in Satoh et al.'s literature (Satoh, K. et al., Nat. Med. 15, 649-656 (2008)). The present inventors treated HUVEC with AngII (1 μM, Wako) at 37° C. in 5% $CO_2$ for 3 hours, washed them with PBS and stained them with 2,7-dichlorofluoroscein diacetate (H2DCF-DA) (5 μM, Cayman) at 37° C. for 30 minutes to visualize the ROS production as green fluorescence (488 nm) through a fluorescence microscope (BIOREVO, Keyence). The relative fluorescence intensity was measured by means of BZ-II analyzer (Keyence) software.

5. Analysis and Quantification of Cardiovascular Hypertrophy

The present inventors conducted all mouse experiments in accordance with experimental protocols that were approved by the Animal Care and Use Committee of the Tohoku University Graduate School of Medicine. The present inventors used an AngII-induced cardiovascular hypertrophy model (see Yagi, S. et al., Circ. Res. 102. 68-76 (2008)) to assess the effect of SmgGDS deficiency on the pleiotropic effects of low-dose statins. The present inventors infused 2.0 mg $kg^{-1}$ $day^{-1}$ or saline for 2 weeks in 10-week-old male $SmgGDS^{+/+}$ littermate control mice and $SmgGDS^{+/-}$ mice. The inventors dissolved AngII in sterile saline and infused it via osmotic mini-pumps (Alzet model 2002, Alze Corp.). The inventors anesthetized the animals with isofluorane. Then, the inventors prepared subcutaneous pockets in the isofluorane-anesthetized mice and placed the pumps into the subcutaneous pockets through a small incision in the back that was closed by suturing. Either statin or vehicle was administered to both the AngII-infused and saline-infused mouse by gavage every day for 2 weeks. All incision sites rapidly healed without any infection. Systolic blood pressure was measured by using a non-invasive tail-cuff system (MK-2000, Muromachi) 2 weeks after the pump implantation. Plasma lipids (triglycerides, total cholesterol, LDL-cholesterol and HDL-cholesterol) were analyzed with the high-performance liquid chromatography system of Skylight Biotech. Echocardiographic analysis was performed by using an ultrasound imaging system (Vevo 2100, VisualSonic Inc.). The mice were shaved and M-mode images of the left ventricle were recorded while the heart rate was kept at about 500 bpm. The percent fractional shortening (FS) and the relative wall thickness were calculated according to Ikeda et al.'s literature (Ikeda, Y. et al., J. Biol. Chem. 280, 29661-29666 (2005)).

6. Plasma Concentrations of Statins

The present inventors measured the plasma concentrations of statins (atorvastatin and pravastatin) after the 2-week treatment in mice, according to Higashi et al.'s literature (Higashi, M. et al., Circ. Res. 93, 767-775 (2003)).

7. Clinical Study on Humans

This protocol was approved by the Human Research Committee of the Tohoku University Graduate School of Medicine and 20 normal healthy human volunteers participated after written consent was obtained (Table 1).

TABLE 1

Baseline characteristics of 20 participants in the human study.

|  | Total (n = 20) |
| --- | --- |
| Age (years) | 30.9 ± 0.7 |
| Gender |  |
| Male, n (%) | 16 (80%) |
| Female, n (%) | 4 (20%) |
| Body weight (kg) | 68.2 ± 2.4 |
| Blood pressure |  |
| Systolic (mmHg) | 124.6 ± 2.2 |
| Diastolic (mmHg) | 77.5 ± 1.5 |
| Heart rate (beats $min^{-1}$) | 72.2 ± 2.3 |

Results are presented as mean ± s.e.m.

The exclusion criteria included abnormal liver or kidney dysfunction before and during the statin administration and treatment. The volunteers received pravastatin (20 mg dayl) or atorvastatin (20 mg $day^{-1}$) orally for 2 weeks in a randomized crossover manner with a 2 weeks washout interval.

8. Statistical Analysis

Comparisons of parameters between two groups were performed with the unpaired Student's t-test. Statistical analysis was performed by one-way ANOVA (analysis of variance) followed by a Dunnett's test. Statistical significance was evaluated with JMP 8 (SAS Institute). A P-value of <0.05 was considered to be statistically significant.

3rd: Results

1. SmgGDS up-regulating Effect of Statins in HUVEC

Figure 1:
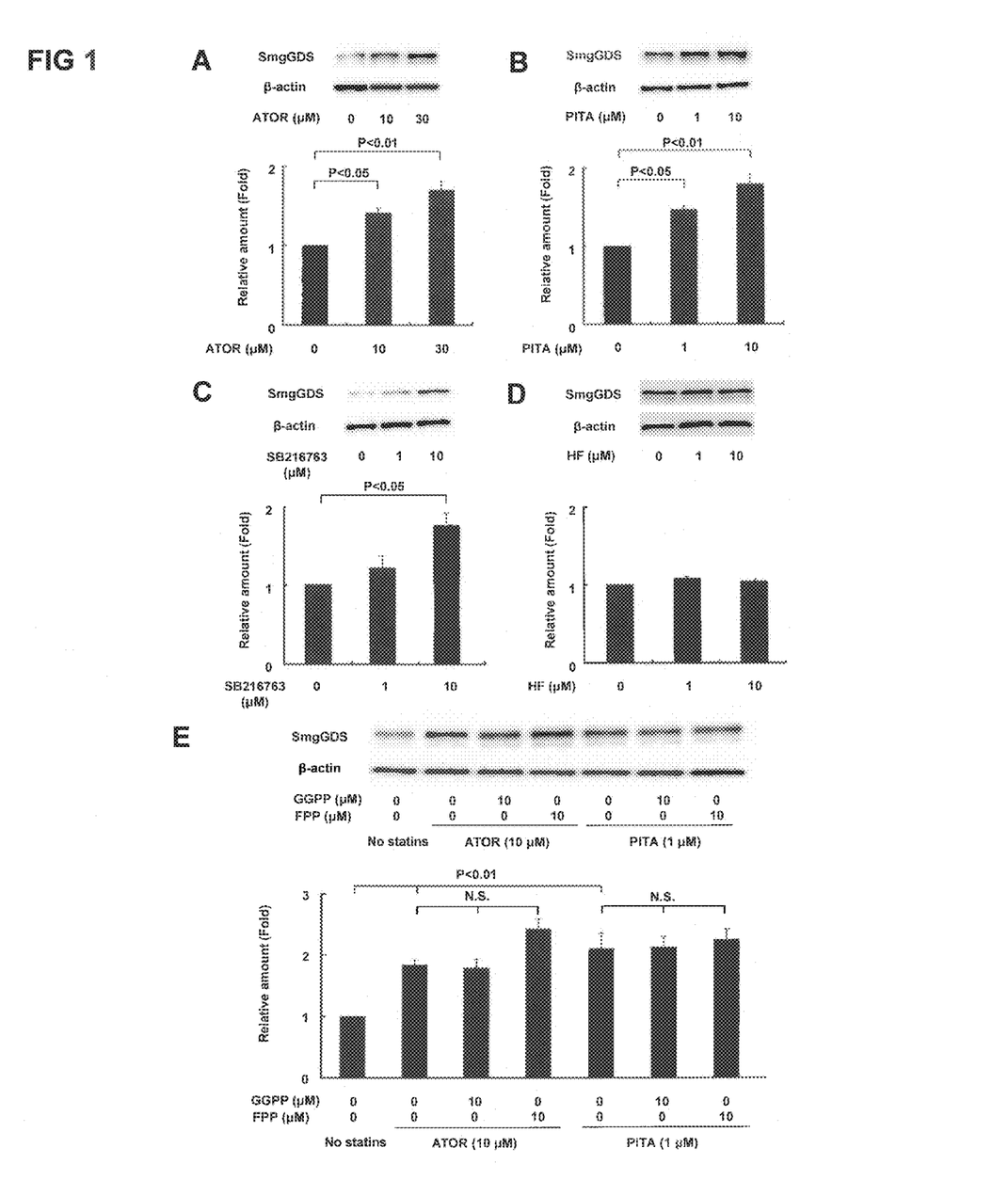
FIG. 1A illustrates that statins increased SmgGDS in HUVEC (human umbilical venous endothelial cells) through the GSK-3β pathway. It represents the expression level of SmgGDS proteins after incubating HUVEC with atorvastatin (ATOR) for 24 hours (n=3). The results are expressed as mean±s.e.m.
FIG. 1B illustrates that statins increased SmgGDS in HUVEC through the GSK-3β pathway. It represents the expression level of SmgGDS proteins after incubating HUVEC with pitavastatin (PITA) for 24 hours (n=3). The results are expressed as mean±s.e.m.
FIG. 1C illustrates that statins increased SmgGDS in HUVEC through the GSK-3β pathway. It represents the expression level of SmgGDS proteins after incubating HUVEC with SB216763, which is a GSK-3β inhibitor, for 24 hours (n=3). The results are expressed as mean±s.e.m.
FIG. 1D illustrates that statins increased SmgGDS in HUVEC through the GSK-3β pathway. It represents the expression level of SmgGDS proteins after incubating HUVEC with a Rho-kinase inhibitor for 24 hours (n=3). The results are expressed as mean±s.e.m.
FIG. 1E illustrates that statins increased SmgGDS in HUVEC through the GSK-3β pathway. It represents the expression level of SmgGDS proteins after incubating HUVEC with farnesyl pyrophosphate (FPP, 10 μM) or geranylgeranyl pyrophosphate (GGPP, 10 μM) in addition to statin (atorvastatin or pitavastatin) for 24 hours (n=3). The results are expressed as mean±s.e.m.

The present inventors examined SmgGDS expression in cultured human umbilical venous endothelial cells (HUVEC) after 24 h treatment with two statins (atorvastatin, 10 and 30 μM and pitavastatin, 1 and 10 μM). These two statins increased SmgGDS expression in HUVEC in a concentration-dependent manner (FIGS. 1A and 1B). This is a novel finding that statins exert class effects to increase SmgGDS expression levels.

Then, the present inventors examined the mechanism by which statins increase SmgGDS expression. There is a report that statins increase β-catenin which, like SmgGDS, is a member of the ARM protein family (see Bergmann, M. W. et al., J. Mol. Cell. Cardiol. 37, 681-690 (2004)). This is achieved through statin-mediated inhibition of glycogen synthase kinase-3β (GSK-3β) and thereby inhibition of β-catenin phosphorylation (see Liu, C. et al., Cell 108, 837-847 (2002) and Salins, P. et al., Neurosci. Lett. 412, 211-216 (2007)). Since phosphorylated β-catenin is more prone to ubiquitination and degradation by means of proteasomes, inhibition of β-catenin phosphorylation increases the stability of β-catenin. It was previously represented that a GSK-3β inhibitor also increases the β-catenin expression level (see Salins, P. et al., Neurosci. Lett. 412, 211-216 (2007)). Thus, the present inventors examined the effect of SB216763, which is a GSK-3β inhibitor, on the SmgGDS expression level in HUVEC. As the inventors expected, SB216763 increased the SmgGDS expression level in a concentration-dependent manner (FIG. 1C).

Next, The present inventors examined the possibility that isoprenoids, such as farnesyl pyrophosphate (FPP) and geranylgeranyl pyrophosphate (GGPP), which are important products in the cholesterol biosynthesis pathway, mediate the statin-induced increase in the SmgGDS expression level (see Goldstein, J. L., Brown, M. S., Nature 343, 425-430 (1990)). Since FPP and GGPP control the post-translational modification of intracellular proteins and the small GTPase membrane localization and their activity, they have been considered to play a central role in the pleiotropic effects of statins (see Van Aelst, L., D' Souza-Schorey, C., Genes Dev. 11, 2295-2322 (1977), Wang, C. Y., Liu, P. Y., Liao. J. K., Trends Mol. Med. 14, 37-44 (2008) and Zhou, Q., Liao, J. K., Circ. J. 74, 818-826 (2010)). It has also been reported that splice variants of SmgGDS control small GTPase prenylation and membrane localization (see Berg, T. J. et al., J. Biol. Chem. 285, 35225-35266 (2010)). Thus, the present inventors examined the effect of FPP and GGPP with statins co-treatment on the SmgGDS expression level in HUVEC. Contrary to the present inventors' expectations, importantly neither FPP nor GGPP inhibited the increase in SmgGDS expression level by statins (FIG. 1B). Thus, it has been proved that the effects of statins to increase the SmgGDS expression level are not mediated through these isoprenoids.

Next, the present inventors examined the possibility that the increased SmgGDS expression level is due to statins' inhibitory effect over the Rho-kinase pathway, since it has been reported that GEF function is regulated by means of Rho-kinase (see Takefuji, M. et al., Biochem. Biophys. Res. Commun. 355, 788-794 (2007)). The present inventors treated HUVEC with hydroxyfasudil (HF), which is a Rho-kinase inhibitor. However, HF did not increase the SmgGDS expression level (FIG. 1C). Thus, the effects of statins to increase the SmgGDS expression level may be not mediated through inhibition of the Rho-kinase pathway. Taken together, these results indicate that statins increase the SmgGDS expression level through inhibition of the GSK-3β pathway.

2. Statins suppress ROS production via SmgGDS

Figure 2:
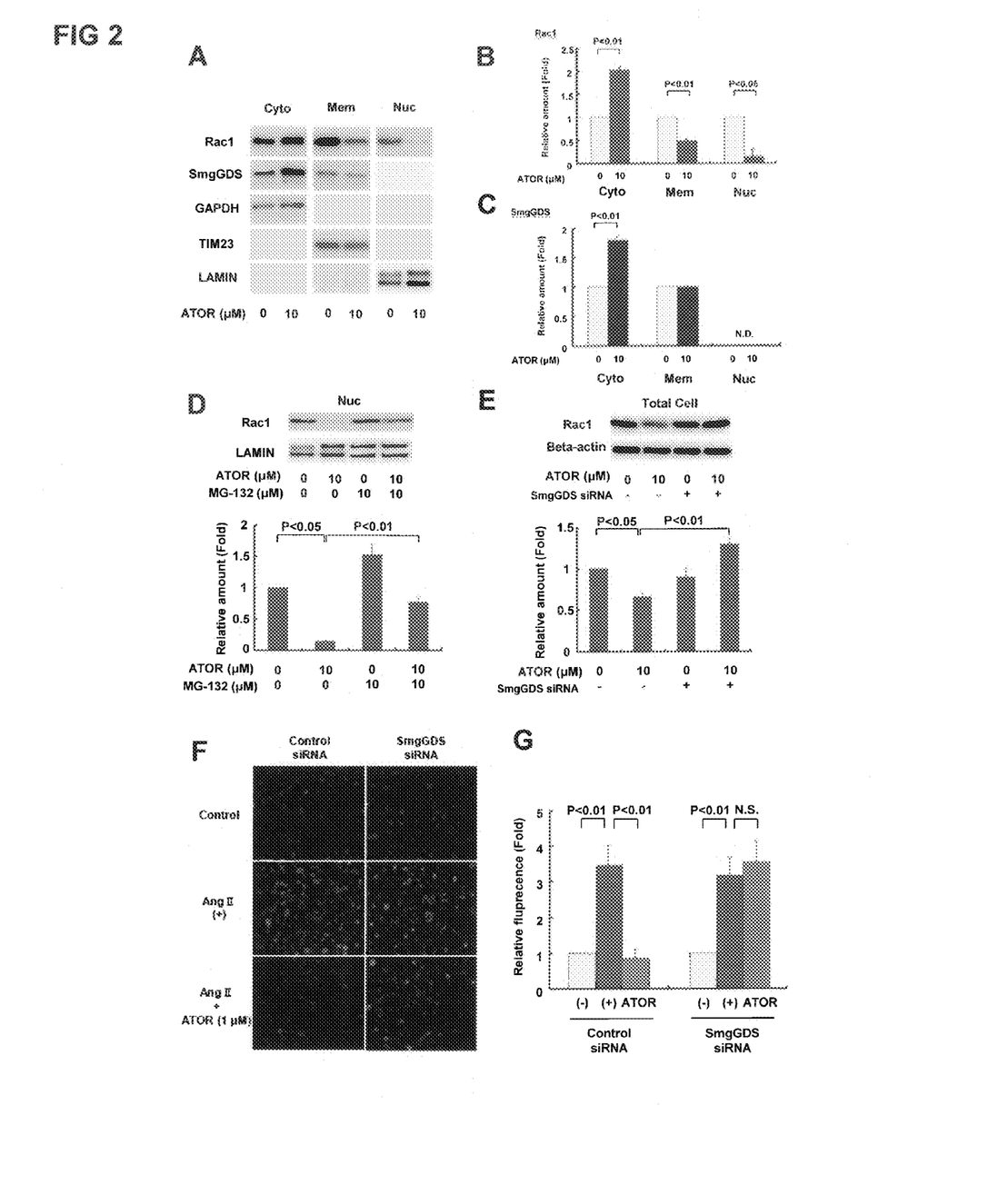
FIG. 2A illustrates the effects of atorvastatin on protein expression in HUVEC subcellular fractions. It represents the results of a western blot analysis after incubation of HUVEC with atorvastatin (ATOR, 10 μM) for 24 hours. Cyto, cytoplasm; Mem, membrane; Nuc, nucleus.
FIG. 2B illustrates the effects of atorvastatin on protein expression in HUVEC subcellular fractions. It represents the results of a quantitative analysis of Rac1 (n=3). The results are expressed as mean±s.e.m.
FIG. 2C illustrates the effects of atorvastatin on protein expression in HUVEC subcellular fractions. It represents the results of a quantitative analysis of SmgGDS (n=3). The results are expressed as mean±s.e.m.
FIG. 2D illustrates the effects of atorvastatin on protein expression in HUVEC subcellular fractions. It represents the effect of a proteasome inhibitor (MG-132) with atorvastatin on Rac1 expression in the nucleus fraction (n=3). The results are expressed as mean±s.e.m.
FIG. 2E illustrates the effects of atorvastatin on protein expression in HUVEC. It represents the results of observing the Rac1 expression level after transfecting a control or SmgGDS siRNA to HUVEC for 48 hours followed by incubating the transfected HUVEC with atorvastatin for 24 hours (n=3). The results are expressed as mean±s.e.m.
FIG. 2F illustrates the effects of atorvastatin on oxidative stress. It represents the results obtained by dichlorofluorescein (DCF) staining of HUVEC after HUVEC were pre-incubated with atorvastatin (1 μM) for 24 hours and then incubated with 1 μM AngII for 3 hours.
FIG. 2G illustrates the effects of atorvastatin on oxidative stress. It represents the result of a quantitative analysis of luminance (n=8). The results are expressed as mean±s.e.m.
Figure 7:
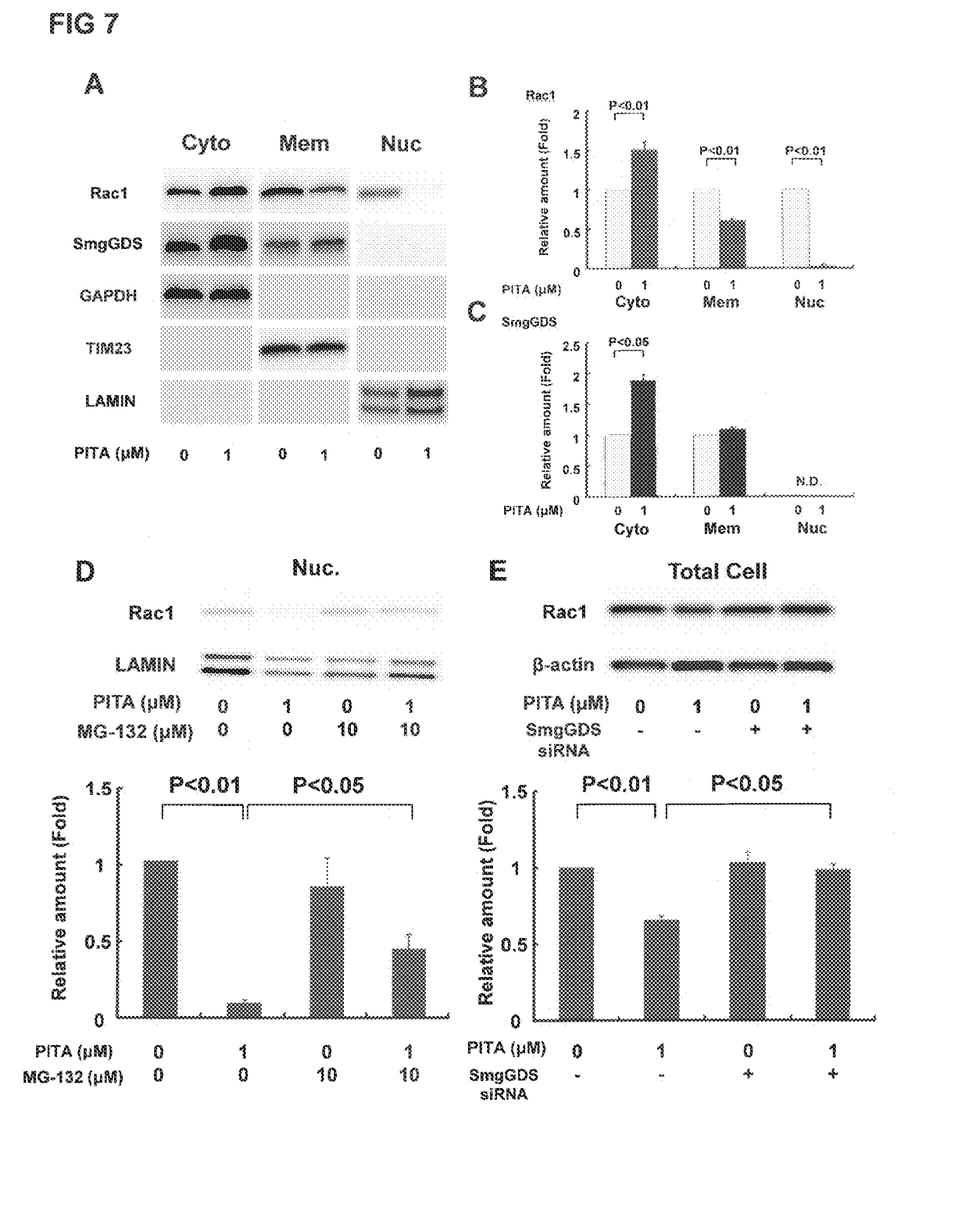
FIG. 7A illustrates the effects of pitavastatin on protein expression in HUVEC subcellular fractions. It represents the results of a western blot analysis after incubation of HUVEC with pitavastatin (PITA, 1 µM) for 24 hours. Cyto, cytoplasm; Mem, membrane; Nuc, nucleus.
FIG. 7B illustrates the effects of pitavastatin on protein expression in HUVEC subcellular fractions. It represents the results of a quantitative analysis of Rac1 and SmgGDS (n=3). The results are expressed as mean±s.e.m.
FIG. 7C illustrates the effects of pitavastatin on protein expression in HUVEC subcellular fractions. It represents the results of a quantitative analysis of SmgGDS (n=3). The results are expressed as mean±s.e.m.
FIG. 7D illustrates the effects of pitavastatin on protein expression in HUVEC subcellular fractions. It represents the effect of co-treating HUVEC with a proteasome inhibitor (MG-132) in addition to pitavastatin on Rac1 expression in the nucleus fraction (n=3). The results are expressed as mean±s.e.m.
FIG. 7E illustrates the effects of pitavastatin on protein expression in HUVEC subcellular fractions. It represents the results of observing the Rac1 expression level after transfecting a control or SmgGDS siRNA to HUVEC for 48 hours followed by incubating the transfected HUVEC with pitavastatin for 24 hours (n=3). The results are expressed as mean±s.e.m.

To investigate the effect of statins on localization and levels of expression of SmgGDS, Rac1 and RhoA in HUVEC, the present inventors examined protein expression levels in the cytoplasm, membrane and nuclear fractions of HUVEC after 24 hour treatment with statins. As a result, it was found that atorvastatin increased the cytoplasmic SmgGDS level and decreased the intra-nuclear Rac1 level (FIGS. 2A to 2C). Pitavastatin also increased the cytoplasmic SmgGDS level and decreased the intra-nuclear Rac1 level (FIGS. 7A to 7C). This is the first report indicating that statins decrease the intra-nuclear Rac1 level.

Next, the present inventors examined the mechanism by which statins decreased the Rac1 level in the nucleus. It has been previously reported that Rac1 is degraded by nuclear proteasome (see Lanning, C. C. et al., J. Biol. Chem. 279, 44197-44210 (2004)). Thus, the present inventors co-treated HUVEC with statins and a proteasomic inhibitor (MG-132). As the present inventors expected, MG-132 inhibited the decreased Rac1 expression level triggered by atorvastatin in the nucleus (FIG. 2D). Similar results were obtained with pitavastatin (FIG. 7C). Thus, it has been proved that statins enhances Rac1 degradation by proteasomes in the nucleus.

Furthermore, the present inventors examined the effect of statins in HUVEC when SmgGDS was knocked down by its siRNA. In control siRNA transfected cells, atorvastatin decreased Rac1 expression level in whole cells (FIG. 2E). However, in SmgGDS siRNA-transfected cells, atorvastatin was no longer able to decrease Rac1 expression level (FIG. 2E). Similar results were obtained with pitavastatin (FIG. 7D). Thus, the present inventors were able to clarify that statins enhance Rac1 degradation via SmgGDS.

Figure 8:
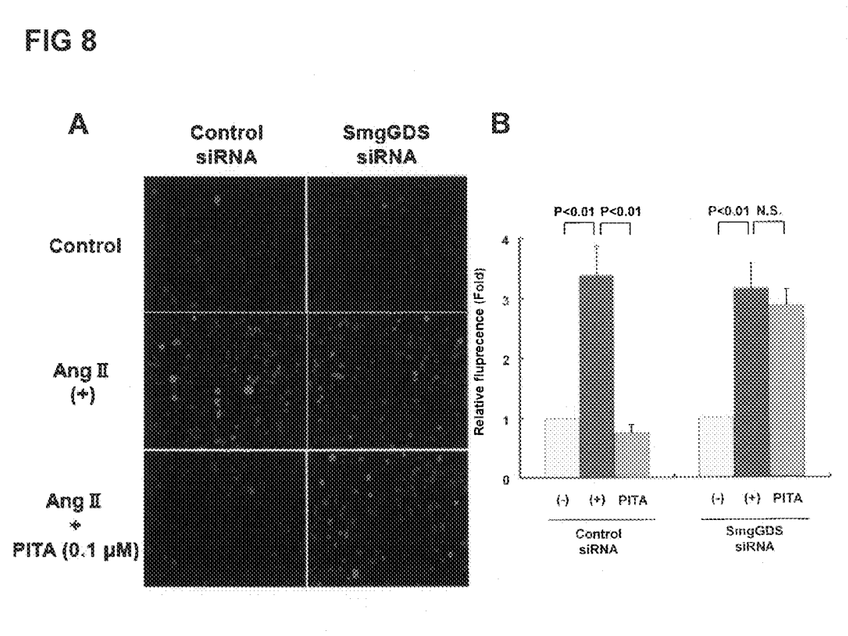
FIG. 8A illustrates the effects of pitavastatin on oxidative stress. It represents the results of dichlorofluorescein (DCF) staining of HUVEC after HUVEC were pre-incubated with pitavastatin (0.1 µM) for 24 hours and then incubated with 1 µM AngII for 3 hours.
FIG. 8B illustrates the effects of pitavastatin on oxidative stress. It represents the result of a quantitative analysis of luminance (n=8). The results are expressed as mean±s.e.m.

Furthermore, the present inventors examined the possible role of Rac1 degradation in mediating the pleiotropic effects of statins by evaluating the anti-oxidative effects of statins. It has been reported that statins decrease AngII-induced production of ROS (see Wassmann, S. et al., Mol. Pharmacol. 59, 646-654 (2001) and Custodis, F., Eberl, M., Kilter, H., Bohm, M., Laufs. U., Cardiovasc. Res. 71, 342-351 (2006)). In control siRNA-transfected cells, atorvastatin (1 μM) decreased the AngII-induced production of ROS (FIGS. 2F and 2G). In contrast, in SmgGDS siRNA-transfected cells, atorvastatin (1 μM) was no longer able to inhibit the AngII-induced production of ROS (FIGS. 2F and 2G). The same results were also obtained with pitavastatin (0.1 μM) (FIGS. 8A and 8B).

3. No Effects of Statins in SmgGDS-Deficient Mice

To investigate whether the effects of statins discovered in vitro also exist in vivo, the present inventors examined the pleiotropic effects of statins on AngII-induced cardiovascular hypertrophy and diastolic dysfunction mice models in vivo.

It has been reported that statins attenuate AngII-induced cardiovascular hypertrophy and diastolic dysfunction in mice without changes in blood pressure or plasma cholesterol levels (see Takemoto M. et al., J. Clin. Invest. 108, 1429-1437 (2001)) and Yagi, S. et al., Circ. Res. 102, 68-76 (2008)). This response is highly likely to depend on the pleiotropic effects of statins.

AngII infusion was administrated to SmgGDS$^{+/-}$ and littermate (SmgGDS$^{+/+}$) mice in a sustained manner for 2 weeks. Systolic blood pressure was elevated in both SmgGDS$^{+/-}$ mice and littermate mice (Table 2).

TABLE 2

Body weight, blood pressure and plasma lipid profiles in mice.

| | SmgGDS$^{+/+}$ | | | | SmgGDS$^{+/-}$ | | | |
| | Control | AngII (+) | AngII + ATOR (10 mpk) | AngII + PRA (50 mpk) | Control | AngII (+) | AngII + ATOR (10 mpk) | AngII + PRA (50 mpk) |
| --- | --- | --- | --- | --- | --- | --- | --- | --- |
| Body weight (g) | 28.2 ± 1.0 | 28.2 ± 1.0 | 27.5 ± 1.1 | 28.2 ± 0.7 | 29.4 ± 0.6 | 27.8 ± 0.8 | 26.9 ± 0.5 | 27.1 ± 1.0 |
| Systolic blood pressure (mmHg) | 119.5 ± 3.6 | 154.5 ± 7.3 | 146.7 ± 7.6 | 141.0 ± 7.3 | 112.5 ± 4.3 | 137.8 ± 9.0 | 140.4 ± 4.4 | 146.7 ± 6.6 |
| Total cholesterol (mg dl$^{-1}$) | 91.2 ± 2.7 | 113.8 ± 21.5 | 98.3 ± 7.7 | 111.2 ± 6.8 | 84.0 ± 5.8 | 109.6 ± 5.7 | 102.3 ± 6.9 | 116.7 ± 5.7 |
| LDL-cholesterol (mg dl$^{-1}$) | 10.7 ± 0.9 | 16.2 ± 4.4 | 13.7 ± 1.6 | 16.1 ± 2.3 | 10.4 ± 1.4 | 12.4 ± 1.1 | 13.6 ± 1.8 | 16.1 ± 1.6 |
| HDL cholesterol (mg dl$^{-1}$) | 74.2 ± 3.4 | 88.3 ± 14.3 | 76.3 ± 6.8 | 88.0 ± 4.5 | 67.1 ± 4.8 | 89.9 ± 4.8 | 81.9 ± 4.8 | 94.0 ± 4.1 |
| Triglyceride (mg dl$^{-1}$) | 52.5 ± 8.3 | 54.2 ± 17.9 | 67.0 ± 11.0 | 47.3 ± 10.9 | 52.0 ± 6.2 | 78.8 ± 13.6 | 81.4 ± 20.1 | 56.6 ± 7.3 |

Results are presented as mean ± s.e.m. (n = 10 each).
AngII, angiotensinII; ATOR, atorvastatin; PRA, pravastatin; LDL, low-density lipoprotein; HDL, high-density lipoprotein.

Additionally, the plasma total and LDL-cholesterol levels represented a rising tendency as a result of the AngII administration (Table 2).

Furthermore, the present inventors administrated each statin by gavage for 2 weeks from the start of AngII administration (advastatin, 10 mg/kg/day or pravastatin, 50 mg/kg/day) to the each group of mouse. The present inventors measured plasma concentration of statins 24 hours after the last administration (Table 3).

TABLE 3

Plasma concentration of statins in mice.

|  | SmgGDS$^{+/+}$ | | SmgGDS$^{+/-}$ | |
| --- | --- | --- | --- | --- |
|  | Ang II + ATOR | Ang II + PRA | Ang II + ATOR | Ang II + PRA |
| atorvastatin (ng ml$^{-1}$) | <0.01 | — | <0.01 | — |
| pravastatin (ng ml$^{-1}$) | — | 0.43 ± 0.08 | — | 0.64 ± 0.24 |

Results are presented as mean ± s.e.m. (n = 6 each).
Ang II, angiotensin II;
ATOR, atorvastatin;
PRA, pravastatin.

The present inventors confirmed that the plasma concentration of statins in mice was equivalent to the 24 hour plasma concentration in humans ($C_{24h}$). There was no significant difference in blood pressure or plasma lipid profile between the vehicle and the statin treatment groups (Table 2).

Figure 3:
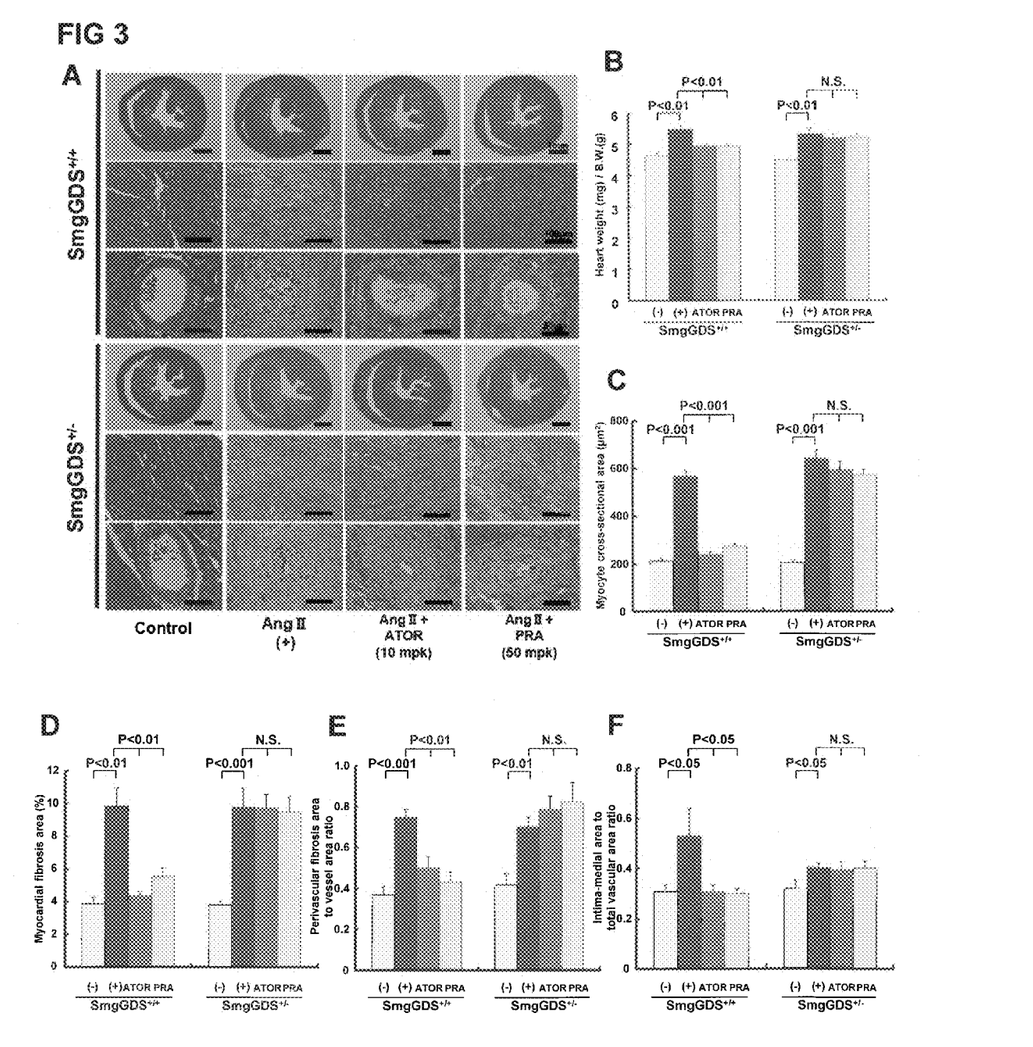
FIG. 3A illustrates that ameliorating effects of statins are absent in SmgGDS-deficient mice with AngII-induced cardiac hypertrophy and fibrosis. It represents Masson's trichrome stained cross-sections of hearts in control (−), AngII-infused mice treated with either atorvastatin (AngII+ATOR, 10 mg kg$^{-1}$ day$^{-1}$) or pravastatin (AngII+PRA, 50 mg kg$^{-1}$ day$^{-1}$), and AngII-infused mice (with administered vehicle, AngII(+)). Myocardial hypertrophy (upper). Interstitial myocardial fibrosis (middle). Fibrosis in perivascular areas of the coronary arteries (lower).
FIG. 3B illustrates that ameliorating effects of statins are absent in SmgGDS-deficient mice with AngII-induced cardiac hypertrophy and fibrosis. It represents that the heart weight/body weight ratio in SmgGDS$^{+/+}$ mice and SmgGDS$^{+/-}$ mice treated with vehicle or statins were determined at 2 weeks after AngII-infusion (n=10). The results are expressed as mean±s.e.m.
FIG. 3C illustrates that ameliorating effects of statins are absent in SmgGDS-deficient mice with AngII-induced cardiac hypertrophy and fibrosis. It represents that the cardiac myocyte cross-sectional area in SmgGDS$^{+/+}$ mice and SmgGDS$^{+/-}$ mice treated with vehicle or statins were determined at 2 weeks after AngII-infusion (n=10). The results are expressed as mean±s.e.m.
FIG. 3D illustrates that ameliorating effects of statins are absent in SmgGDS-deficient mice with AngII-induced cardiac hypertrophy and fibrosis. It represents the results of a quantitative analysis of interstitial myocardial fibrosis (n=10). The results are expressed as mean±s.e.m.
FIG. 3E illustrates that ameliorating effects of statins are absent in SmgGDS-deficient mice with AngII-induced cardiac hypertrophy and fibrosis. It represents the results of a quantitative analysis of fibrosis in perivascular areas (n=10). The results are expressed as mean±s.e.m.
FIG. 3F illustrates that ameliorating effects of statins are absent in SmgGDS-deficient mice with AngII-induced cardiac hypertrophy and fibrosis. It represents the results of a quantitative analysis of cardiovascular remodeling (n=10). The results are expressed as mean±s.e.m.
Figure 4:
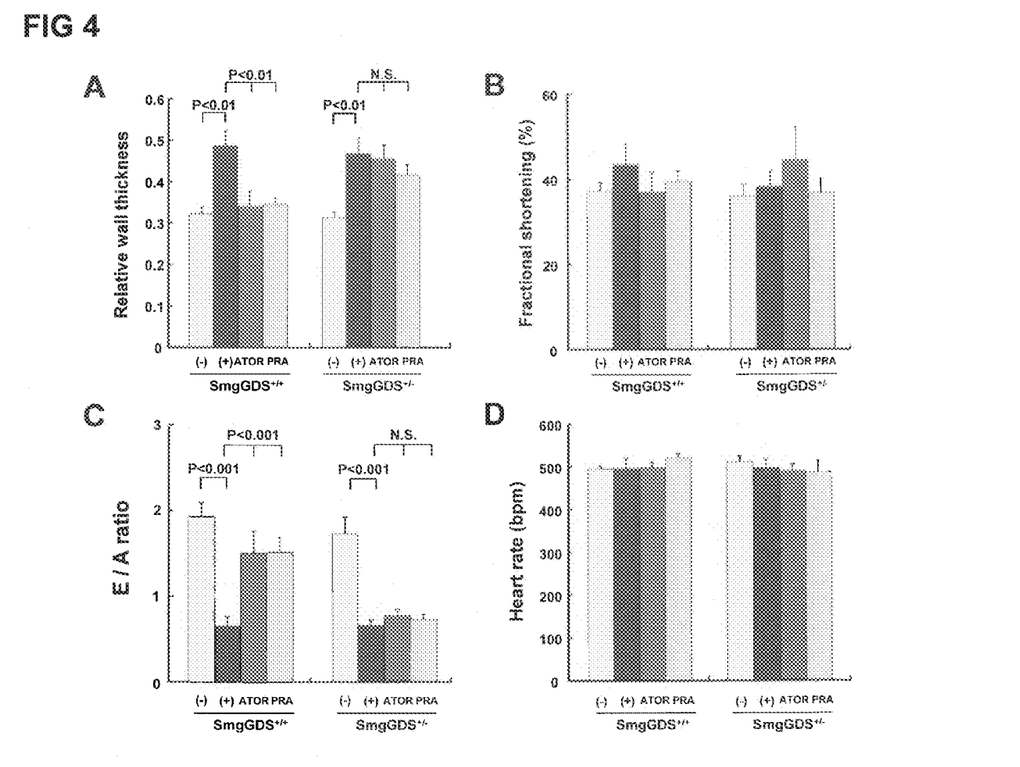

Analysis of heart weight and microscopic examination of heart sections revealed that AngII induced cardiomyocyte and myocardial hypertrophy and remarkably triggered interstitial fibrosis, perivascular fibrosis and thickening of coronary arteries (FIGS. 3A to 3C). In littermate mice, the protective effects of statins against AngII-induced cardiovascular hypertrophy and fibrosis were noted. However, no protective effects of statins were observed in SmgGDS$^{+/-}$ mice (FIGS. 3A to 3F). Furthermore, the present inventors evaluated cardiac performance of these mice, using ultrasonography (FIGS. 4A to 4D). Although LV fractional shortening (LVFS), which is a marker of LV systolic function, was not significantly influenced by either AngII or statin treatment (FIG. 4B), AngII administration significantly attenuated LV diastolic function as indicated by a lowered E to A wave velocity ratio, which is a marker of LV diastolic function, in both control and SmgGDS$^{+/-}$ mouse (FIG. 4C). In contrast, statin treatment ameliorated the impairment in LV diastolic function caused by AngII (FIG. 4C). In SmgGDS$^{+/-}$ mice, the beneficial effects of statins on LV diastolic dysfunction were absent (FIG. 4C).

4. Effects of Statins on SmgGDS in Humans

Figure 9:
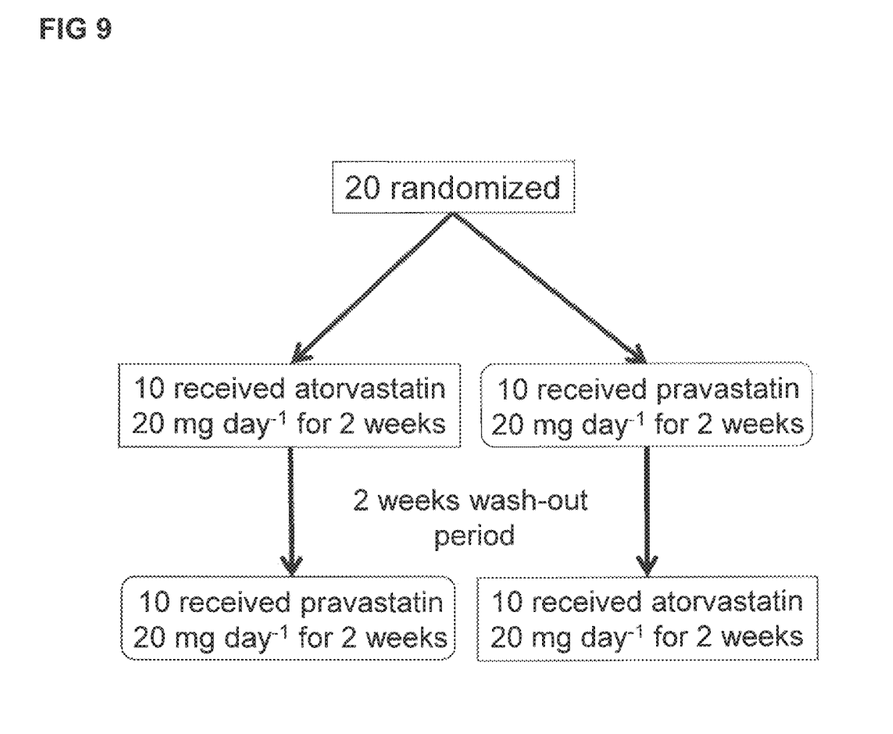
FIG. 9 illustrates a flowchart of an experiment plan for clinical researches.

Finally, the present inventors examined the effects of statins on SmgGDS expression in normal healthy adult volunteers, who received pravastatin and atorvastatin (20 mg day$^{-1}$ each) orally for 2 weeks (FIG. 9). The both statins reduced the concentration level of total cholesterol and that of LDL-cholesterol in blood even in the normal and healthy adult volunteers (Table 4).

TABLE 4

Effects of statins on plasma lipid profiles, glucose, insulin and HOMA-IR.

| | Pravastatin 20 mg day$^{-1}$ | | | | Atorvastatin 20 mg day$^{-1}$ | | | |
| --- | --- | --- | --- | --- | --- | --- | --- | --- |
| Fasting lipids (mg dl$^{-1}$) | Baseline | After 2 weeks | Change (%) | P value | Baseline | After 2 weeks | Change (%) | P value |
| Total cholesterol | 192 ± 4.5 | 165 ± 4.5 | −14 | <0.001 | 197 ± 5.0 | 138 ± 3.8 | −30 | <0.001 |
| LDL-cholesterol | 116 ± 4.5 | 88 ± 4.0 | −24 | <0.001 | 118 ± 4.3 | 64 ± 3.4 | −46 | <0.001 |
| HDL-cholesterol | 58 ± 2.7 | 61 ± 2.8 | 5 | <0.05 | 60 ± 2.9 | 60 ± 2.7 | 0 | N.S. |
| Triglyceride | 103 ± 12.9 | 87 ± 9.1 | −16 | N.S. | 109 ± 9.9 | 73 ± 6.5 | −33 | <0.001 |
| RLP cholesterol | 4.1 ± 0.5 | 3.2 ± 0.3 | −22 | <0.05 | 4.0 ± 0.3 | 2.6 ± 0.1 | −35 | <0.001 |
| MDA-LDL (U l$^{-1}$) | 113 ± 9.6 | 85 ± 6.7 | −25 | <0.01 | 118 ± 10.6 | 73 ± 4.5 | −38 | <0.001 |
| Glucose (mg dl$^{-1}$) | 96 ± 1.4 | 99 ± 1.3 | 3 | N.S. | 97 ± 1.3 | 98 ± 1.5 | 1 | N.S. |
| Insulin (μIU ml$^{-1}$) | 9.4 ± 1.1 | 8.4 ± 0.9 | −11 | N.S. | 8.8 ± 0.8 | 8.3 ± 0.5 | −6 | N.S. |
| HOMA-IR | 2.2 ± 0.3 | 2.1 ± 0.2 | 5 | N.S. | 2.1 ± 0.2 | 2.0 ± 0.1 | −5 | N.S. |

Results are presented as mean ± s.e.m. (n = 20 each).
LDL, low-density lipoprotein; HDL, high-density lipoprotein; RLP, remnant like particle; HOMA-IR, homeostasis model assessment-insulin resistance.

SmgGDS expression in leukocytes in circulating blood was significantly increased after the treatment with pravastatin or atorvastatin (FIG. 5A). In average of the 20 volunteers, SmgGDS increased by about 1.4 times as a result of treatment with 20 mg of pravastatin and by about 1.5 times as a result of treatment with 20 mg of atrovastatin. Additionally, it was confirmed that 4 volunteers who did not represented any increase in SmgGDS as a result of treatment with 10 mg of pravastatin in a preliminary administrative session represented an increase of SmgGDS as a result of treatment with 20 mg of pravastatin. Likewise, 3 volunteers out of the above 4 volunteers showed an increase of SmgGDS after switching from pravastatin to atorvastatin. Note that, because the LDL-cholesterol level fell in the 4 volunteers, it is not necessary to increase the statin dose or use an alternative statin for all of them if hypercholesterolemia is the object of therapy. It is interesting to note that both pravastatin (a hydrophilic statin) and atorvastatin (a lipophilic statin) exerted a comparable incremental effect on SmgGDS expression level in humans, suggesting a class effect of statins in the increased SmgGDS expression level in humans.

Furthermore, malondialdehyde-modified (MDA)-LDL-cholesterol, which is one of the oxidative stress markers, was decreased with the statin treatment (Table 4). Importantly, a significant negative correlation was recognized between the extent of change in the SmgGDS level and the MDA-LDL-cholesterol level, whereas no significant correlation was recognized with total or LDL-cholesterol (FIGS. 5B to 5E).

The invention claimed is:

1. A method of increasing the dose of a statin to a human patient suffering from a cardiovascular disease comprising:
   Step (1) measuring SmgGDS expression level in leukocytes of the patient suffering from a cardiovascular disease with the use of an anti SmgGDS antibody before administration of a statin;
   Step (2) administering a statin to the patient;
   Step (3) measuring SmgGDS expression level in leukocytes of the patient with the use of an anti SmgGDS antibody after administration of the statin;
   Step (4) comparing the expression level measured in Step (1) to the expression level measured in Step (3) and detecting an SmgGDS expression level measured in Step (3) that is less than 1.4 times the SmgGDS expression level measured in Step (1); and
   Step (5) administering a statin dose to the patient that is increased by 10 mg as compared to the statin administered in Step (2).

2. The method of increasing the dose of a statin according to claim 1, wherein the cardiovascular disease is cardiovascular hypertrophy, cardiomyocyte hypertrophy, cardiovascular fibrosis, coronary arteriosclerosis, hypertension or heart failure.

3. The method of increasing the dose of a statin according to claim 1, wherein the statin is selected from the group consisting of atorvastatin, dihydrocompactin, bervastatin, carvastatin, cerivastatin, crilvastatin, dalvastatin, fluvastatin, glenvastatin, fluindostatin, velostatin, lovastatin, mevastatin, compactin, pitavastatin, pravastatin, rivastatin, rosuvastatin, simvastatin, sirrivastatin, CI-981 and pharmacologically acceptable salts thereof.

4. The method of increasing the dose of a statin according to claim 1, wherein the cardiovascular disease is cardiovascular hypertrophy.

5. The method of increasing the dose of a statin according to claim 1, wherein the statin is atorvastatin.

* * * * *